United States Patent [19]

Urry et al.

[11] Patent Number: 4,693,718
[45] Date of Patent: Sep. 15, 1987

[54] STIMULATION OF CHEMOTAXIS BY CHEMOTACTIC PEPTIDES

[75] Inventors: Dan W. Urry; Marianna M. Long, both of Birmingham, Ala.

[73] Assignee: University of Alabama in Birmingham, Birmingham, Ala.

[21] Appl. No.: 793,225

[22] Filed: Oct. 31, 1985

[51] Int. Cl.$^4$ ............................ A61F 2/02; A01N 1/02
[52] U.S. Cl. ........................................ 623/11; 623/66; 427/2; 530/328
[58] Field of Search ........................ 530/328; 514/15; 623/66, 1, 16, 11; 427/2; 106/124

[56] References Cited

U.S. PATENT DOCUMENTS 4,605,413  8/1986  Urry et al. ........................ 623/66 X

OTHER PUBLICATIONS

Senior et al., "Chemotactic Responses of Fibroblasts to Tropoelastin and Elastin Derived Peptides", J. Clin. Invest., vol. 70, Sep. 1982, pp. 614-618.

Mecham et al., "Appearance of Chemostactic Responsiveness to Elastin Peptides by Developing Fetal Bovine Ligament Fibroblasts Parallels the Onset of Elastin Production", J. Cell Biol., vol. 98, May 1984, 1813-1816.

Sandberg et al., "Elastin Covalent Structure as Determined by Solid Phase Amino Acid Sequencing," Path. Biol., 1985, 33, No. 4, 266-274.

*Primary Examiner*—Richard J. Apley
*Assistant Examiner*—Alan W. Cannon
*Attorney, Agent, or Firm*—Oblon, Fisher, Spivak, McClelland & Maier

[57] ABSTRACT

A method of stimulating chemotaxis toward a prosthetic device is disclosed, which method comprises incorporating a chemotactic peptide of the formula $$B^1\text{-}X\text{-}(AGVPGFGVG)_n\text{-}Y\text{-}B^2$$

wherein
A is a peptide-forming residue of L-alanine:
P is a peptide-forming residue of L-proline;
G is a peptide-forming residue of glycine;
V is a peptide-forming residue of L-valine;
F is a peptide-forming residue of L-phenylalanine;
$B^1$ is H or a biocompatible N-terminal group;
$B^2$ is OH, $OB^3$ where $B^3$ is a non-toxic metal ion, or a biocompatible C-terminal group:
X is GVPGFGVG, VPGFGVG, PGFGVG, GFGVG, FGVG, GVG, VG, G or a covalent bond;
Y is AGVPGFGV, AGVPGFG, AGVPGF, AGVPG, AGVP, AGV, AG, A or a covalent bond; and
n is an integer from 1 to 100;

into a surface of the prosthetic device. Prosthetic devices which have the property of enhancing invasion of elastic fiber synthesizing fibroblasts as a result of the chemotactic peptide are also disclosed.

10 Claims, 4 Drawing Figures

STIMULATION OF CHEMOTAXIS BY CHEMOTACTIC PEPTIDES

BACKGROUND OF THE INVENTION

This work was supported in part by grants from the National Institutes of Health and the Government has certain rights in the invention as a result of this support.

1. Field of the Invention

This invention relates to stimulation of chemotaxis, particularly in relation to prosthetic devices.

2. Description of the Prior Art

Replacement of a blood vessel by a prosthetic device is an important and common practice in modern vascular surgery. Although some use is made of veins or arteries taken from other portions of a patient's body, most of such prosthetic devices are prepared from artificial materials that can be prepared in a variety of sizes and stored in a sterile state ready for use.

There are several essential properties of cardiovascular prosthetic materials, among which are the following:

1. Retardation of thrombosis and thromboembolism (antithrombogenic);
2. Minimal harm to blood cells and minimal blood cell adhesion;
3. Long life as prosthetic inserts: and
4. High compliance with the physical and chemical properties of natural blood vessel such as similar elastic modulus and tensile strength.

Another useful property would be a chemotaxis that induced rapid endothelialization and invasion of connective tissue cells for vascular wall reconstruction in a manner such that the prosthesis would be slowly replaced by and/or integrated into newly synthesized internal elastic lamina. None of the materials presently being used can fulfill all of these requirements.

The most commonly used fabric for blood vessel prosthesis is made from Dacron (Trademark, DuPont), a synthetic polyester fiber made from polyethylene terephthalate. Dacron has been used in several weaves and in combination with other materials. An example of a frequently used material is the DeBakey Elastic Dacron fabric manufactured by USCI, a division of C.R. Bard, Inc. (Cat. No. 007830). Other commonly used materials are felted polyurethane and polytetrafluoroethylene (Berkowitz et al, Surgery, 72, 221 (1972); Wagner et al, J. Surg. Res., 1, 53 (1956); Goldfarb et al, Trans Am. Soc. Art. Int. Org., XXIII, 268 (1977)). No chemotactic substance is normally used with these materials.

Another recent development in prosthetic devices is artificial skin of the type disclosed in Yannas and Burke, J. Biomed. Mat. Res., 14, 65–81 (1980). The artificial skin is a collagen/glycosaminoglycan (GAG) composite and had been successfully tested as full-thickness skin wound replacements. Such membranes have effectively protected wounds from infection and fluid loss for long periods of time without rejection and without requiring change or other invasive manipulation. Appropriately designed artificial skin of this type has retarded the wound contraction, and the artificial skin has been replaced, at least in part, by newly synthesized connective tissue. Additional disclosure of this artificial skin is found in Yannas et al, ibid, 107–131 (1980), and Dagalakis et al, ibid, 511–528 (1980). No chemotactic substance is normally used with these materials.

One chemotactic material that might be useful in enhancing invasion of fibroblasts into such prosthetic devices is platelet-derived growth factor (PDGF), a potent fibroblast chemo-attractant. Unfortunately, PDGF cannot be synthesized and must be obtained from platelets, making the utilization of such a material on a wide scale impractical.

Recently, a chemotactic peptide has been identified in tropoelastin and is described in U.S. patent application Ser. No. 533,670. This material is a chemotactic peptide having a 6-amino-acid repeating unit of formula APGVGV in which A represents alanine, P represents proline, G represents glycine, and V represents valine. Although this material readily produces chemotaxis and is a natural component of the human body, therefore making it particularly suitable for use in vivo, room remains for additional improvements in the field of chemotactic stimulation.

Accordingly, there remains a need for an artificial and easily synthesized chemotactic material capable of attracting fibroblasts into prosthetic devices and thereby enhancing the incorporation of such devices into the regenerating natural tissue.

SUMMARY OF THE INVENTION

Accordingly, it is an object of this invention to provide an artificial material having chemotactic properties towards fibroblasts.

It is a further object of this invention to provide a prosthetic device which is readily incorporated into regenerating tissue, such as skin or blood vessel walls.

It is still another object of this invention to provide a chemotactic material having stimulating activity to a greater extent than was previously available.

These and other objects of the invention as will hereinafter become more readily apparent have been accomplished by providing a method of stimulating chemotaxis, which comprises: incorporating a chemotactic peptide of the formula $$B^1\text{-}X\text{-}(AGVPGFGVG)_n\text{-}Y\text{-}B^2$$

wherein
A is a peptide-forming residue of L-alanine;
P is a peptide-forming residue of L-proline;
G is a peptide-forming residue of glycine;
V is a peptide-forming residue of L-valine;
F is a peptide-forming residue of L-phenylalanine;
$B^1$ is H or a biocompatible N-terminal group;
$B^2$ is OH, $OB^3$ where $B^3$ is a non-toxic metal ion, or a biocompatible C-terminal group:
X is GVPGFGVG, VPGFGVG, PGFGVG, GFGVG, FGVG, GVG, VG, G or a covalent bond;
Y is AGVPGFGV, AGVPGFG, AGVPGF, AGVPG, AGVP, AGV, AG, A or a covalent bond; and
n is an interger from 1 to 100;
into a surface of a prosthetic device in an amount sufficient to increase chemotaxis towards said surface.

This invention also comprises chemotactic surfaces and prosthetic devices prepared according to the method set forth above.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein.

DESCRIPTION OF THE PREFERRED EMBODIMENTS

The present invention arose as the result of investigations into the structure of elastic fibers present in blood vessel walls and other elastic materials, such as ligaments, present in humans and animals. The central portion of the elastic fibers of vascular wall, skin, lung and ligament is derived from a single protein called tropoelastin. Polypeptide sequences of tropoelastin from vascular wall have been shown by Sandberg and colleagues to contain a repeat hexapeptide (Ala-Pro-Gly-Val-Gly-Val)$_n$, a repeat pentapeptide (Val-Pro-Gly-Val-Gly)$_n$, and a repeat tetrapeptide (Val-Pro-Gly-Gly)$_n$, where Ala, Pro, Val and Gly respectively represent alanine, proline, valine and glycine amino acid residues. (Peptide representations in this application conform to the standard practice of writing the NH$_2$-terminal amino acid residue at the left of the formula and the CO$_2$H-terminal amino acid residue at the right.) A high polymer of the hexapeptide has been synthesized, whereby it forms cellophane-like sheets. The hexapeptide has therefore been thought to fill a structural role in the natural material.

However, recent investigations have been indicated that this hexapeptide and permutations of this sequence are chemotactic for fibroblasts which synthesize elastic fiber precursor protein in biological systems. As a result of this discovery and related investigations into the various permutations of the natural material, U.S. patent application Ser. No. 533,670 was filed disclosing and claiming a synthetic material based on the hexapeptide sequence.

Further investigations into tropoelastin have revealed the presence of a nonapeptide that repeats four times in a single continuous sequence. Investigations into the property of materials based on this repeating unit had indicated that synthetic materials produced having this sequence are potent chemotactic agents having an activity even higher than synthetic materials based on the previously discovered hexapeptide sequence. At their maximum activity, the nonapeptides are as active as platelet-derived growth factor (PDGF) at 30 ng/ml. The nonapeptides therefore are fully as potent as the previously discovered hexapeptides and achieve this activity at a comparable or slightly lower concentration. It is expected that enhanced invasion of elastic-fiber-synthesizing fibroblasts will occur when a prosthetic device, designed for incorporation into regenerating tissue, is treated by incorporating a chemotactic peptide of the formula B$^1$-X-(AGVPGFGVG)$_n$-Y-B$^2$ wherein
A is a peptide-forming residue of L-alanine:
P is a peptide-forming residue of L-proline;
G is a peptide-forming residue of glycine;
V is a peptide-forming residue of L-valine;
F is a peptide-forming residue of L-phenylalanine;
B$^1$ is H or a biocompatible N-terminal group;
B$^2$ is OH, OB$^3$ where B$^3$ is a non-toxic metal ion, or a biocompatible C-terminal group:
X is GVPGFGVG, VPGFGVG, PGFGVG, GFGVG, FGVG, GVG, VG, G or a covalent bond;
Y is AGVPGFGV, AGVPGFG, AGVPGF, AGVPG, AGVP, AGV, AG, A or a covalent bond; and
n is an integer from 1 to 100;
into a surface of the prosthetic device. In this way the surface of the prosthetic device becomes the source of a concentration gradient of the chemotactic peptide.

Both the isolated nonamers, such as H-AGVPGFGVG-OH, and polynonapeptides have the chemotactic property. The nonapeptide H-GFGVGAGVP-OH has been shown to have essentially the same chemotactic activity as H-AGVPGFGVG-OH. Chemotactic activity is also expected for the other permutations; i.e., H-GVPGFGVGA-OH, H-VPGFGVGAG-OH, H-PGFGVGAGV-OH, H-FGVGAGVPG-OH, H-GVGAGVPGF-OH, H-VGAGVPGFG-OH, and H-GAGVPGFGV-OH. When a polynonapeptide is present, the compound (perhaps in the form of fragments derived therefrom by in vivo enzymatic action) is chemotactic regardless of the value of n. However, for ease of handling, values of n of no more than 100 are preferred since higher molecular weight compounds have limited solubility and are difficult to handle. Preferred are values of n from 1 to 10, with values of about 5 being most preferred.

It will be noted that polynonapeptides can be synthesized using any of the nonapeptide "monomers" listed above. Thus, polynonapeptides generally will have the structure B$^1$-(repeating unit)$_n$-B$^2$ where B$^1$ and B$^2$ represent end groups which are discussed later. The repeating unit can be any of the permutations of the nonamer listed above. In fact, if the chemotactic peptide is not synthesized from nonapeptide "monomers" but rather is synthesized by sequential addition of amino acids to a growing peptide (such as in an automatic peptide synthesizer or by use of an artificial gene) the designation of a repeating unit is somewhat arbitrary. For example, the peptide H-GFGVGAPVPGFGVGAPVPGFG-VGAPVPGF-OH can be considered to consist of any of the following repeating units and end groups, among others: H-(GFGVGAPVP)$_3$-GF-OH, H-G-(FGVGAPVPG)$_3$-F-OH, H-GF-(GVGAPVPGF)$_4$-OH, H-GFG-(VGAPVPGFG)$_2$-VGAPVPGF-OH, H-GFGV-(GAPVPGFGV)$_2$-GAPVPGF-OH, or H-GFGVG-(APVPGFGVG)$_2$-APVPGF-OH.

Synthesis of the chemotactic peptide is straight-forward and easily accomplished by a protein chemist. The resulting peptides generally have the structure B$^1$-(repeating unit)$_n$-B$^1$ where B$^1$ and B$^2$ represent any chemically compatible end group on the amino and carboxyl ends of the molecule, respectively, and n is an integer from 1 to about 100. When B$^1$ is H, B$^2$ is OH, and n=1, the compound is the nonapeptide itself. When n is greater than 1, the compound is a polynonapeptide (often referred to herein as a polypeptide). It is possible that one or more amino acid residue or segment of amino acid residues not present in the normal polynonapeptide sequence may be interspersed within a polynonapeptide chain so long as the chemotactic character of the resulting molecule is not completely disrupted. As clearly indicated by the formula and by the following discussion, the invention encompasses incorporation of a nonamer or polynonapeptide into a larger peptide chain in which $B^1$ and $B^2$ represent the remainder of the larger peptide chain.

Other examples of terminal $B^1$ and $B^2$ end groups include portions of the repeating peptide units themselves with free amino or carboxylic acid groups or salts thereof, free amino or carboxylic acid groups or salts (especially alkali metal salts), and peptide or amino acid units that have retained a blocking group that was present during synthesis of the polypeptide or that have a biocompatible group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule. The end groups are not critical and can be any organic or inorganic group that does not destroy the chemotactic properties of the polypeptide or confer bio-incompatibility to the molecule as a whole. The term biologically compatible as used in this application means that the component in question will not harm the organism in which it is implanted to such a degree that implantation is as harmful as or more harmful than the needed prosthetic device.

Methods of preparing polypeptide polymers have been disclosed in Rapaka and Urry, *Int. J. Peptide Protein Res.*, 11, 97 (1978), Urry et al, *Biochemistry*, 13, 609 (1974), and Urry et al, *J. Mol. Biol.*, 96, 101 (1975), which are herein incorporated by reference. The synthesis of these peptides is straightforward and can be easily modified to any of the peptides disclosed herein. The following summary, which is not to be considered limiting, is an example of the general method of synthesizing the polypeptides.

The first step in the formation of a polynonapeptide of the invention usually is synthesis of a nonapeptide monomer. Any of the classical methods of producing peptide molecules may be used in synthesizing the building blocks of the polymers of the present invention. For example, synthesis can be carried out by classical solution techniques starting from the C-terminal aminio acid as a benzyl (Bzl) ester p-tosylate. Each successive amino acid is then coupled to the growing peptide chain by means of its water-soluble carbodiimide and 1-hydroxybenzotriazole. A typically used carbodiimide is 1-(3-dimethylaminopropyl)-3-ethylcarbodiimide hydrochloride (EDCI). During the coupling reaction the amino group is protected. The protecting group is then removed after condensation has taken place. A suitable protecting group is tert-butyloxycarbonyl (Boc), which can easily be removed by trifluoroacetic acid.

The first product obtained in the synthesis of the hexapeptide monomer is a protected nonapeptide, such as Boc-L·Ala-Gly-L·Val-L·Pro-Gly-L·Phe-Gly-L·Val-Gly-OBzl. This protected monomer is converted into the reactive monomer by, for example, replacement of the benzyl ester with the p-nitrophenyl ester, for example by effectively exchanging with p-nitrophenyl trifluoroacetate, and removal of the Boc protecting group. The resulting reactive monomer is polymerized, in the presence of a base such as triethylamine as necessary, to give the polypeptide. A blocking group, such as H-Val-OMe may be added at the conclusion of the polymerization reaction to convert the remaining reactive p-nitropnenyl esters to non-reactive terminal groups if desired.

Since all of the amino acids present in the polypeptides of the invention have corresponding DNA codons, the polypeptides can also be produced by genetic engineering using synthetic genes containing codons that correspond to the desired amino acid sequence.

When a modified chemical structure is desired, as, for example, when chemical cross-linking between two chains of polynonapeptide or between a polynonapeptide chain and a peptide-forming part of the structure of a prosthetic device will be carried out, side-group-blocked lysine or glutamic acid (or another amino acid with a protected side group capable of forming a cross-link after the protecting group is removed) may be utilized in place of one of the normal amino acids that is present in the polypeptide chain. A synthesis of a chemically cross-linked polypentapeptide of similar structure is disclosed in U.S. Pat. No. 4,187,852, which is herein incorporated by reference.

It is not necessary for the chemotactic peptide of the invention to be covalently attached to the surface toward which chemotaxis is being stimulated. It is sufficient that the peptide be present at the surface. Therefore, the phrase "incorporating into a surface" as used in this application encompasses all methods of applying a chemotactic peptide of this invention to a surface, whether that application results in chemical bonding or not. For example, solutions or suspensions containing the peptide can be painted on the surface of a prosthetic device or a device can be submerged in a solution of the chemotactic peptide.

It is also possible to form covalent bonds between the chemotactic peptide and the prosthetic device. For example, during the synthesis of a chemotactic peptide as described above, various intermediates are produced which have reactive carboxy or amino terminals. Many of the prosthetic devices which are intended for incorporation into regenerating tissue are prepared from collagen or related materials and therefore contain free amino acid functional groups, such as amino or carboxylic acid groups. Peptide bonds can easily be formed between such functional groups in the prosthetic device and reactive intermediates such as those described above.

The type of prosthetic device which can be used in conjunction with the present invention is not limited, since the chemotactic property is related to the peptide and not to the prosthetic device itself. It is preferred, however, that the prosthetic device be one which is intended for incorporation into regenerating tissue, such as an artificial vein or artery or artificial skin. Publications which disclose various prosthetic devices useful for forming artificial skin or blood vessel walls are listed in the section of this application entitled Background of the Invention, and these publications are herein incorporated by reference. Two particularly preferred embodiments of the present invention involve using the chemotaxic polypeptide with a collagen/glycosaminoglycan composite material as an artificial skin, as described in U.S. Pat. No. 4,280,954, and with biocompatible artificial materials based on polypeptides as described in U.S. Pat. No. 4,187,852: U.S. patent application Ser. No. 308,091, filed Oct. 2, 1981; and U.S. patent application Ser. No. 452,801, filed Dec. 23, 1982, all of which are herein incorporated by reference. These are peptite-containing materials, and the chemotactic polypeptide may readily be attached by covalent bonding into such materials by the methods described above. However, as also previously indicated, covalent bonding is not necessary and indeed is not preferred since the chemotactic property is also exhibited when the chemotactic peptide is merely present on the surface or in the pores of a prosthetic material. Prosthetic devices having surfaces comprising other structural peptides are also preferred over prosthetic devices having other types of surfaces, although other types of surfaces, such as Dacron, and other synthetic fibers, are specifically included. Examples include natural materials such tendons or ligaments (for example, those transferred from one location to another within the same body) and synthetic or semi-synthetic materials. Semi-synthetic materials are those derived by manipulation of natural materials, such as collagen.

The amount of chemotactic peptide which is required for a particular prosthetic device can easily be determined by simple experimentation. Generally, quite low concentrations of the chemotactic peptide are required. For example, doping of a non-chemotactic surface to produce low concentrations of 0.1 nM to 100 nM of a chemotactic peptide at the surface will be sufficient. Generally, from $10^{-9}$ to $10^{-3}$ millimoles of hexamer or repeating unit of a polyhexapeptide per 100 cm$^2$ of surface is sufficient for this purpose. It is preferred to produce a concentration of the chemotactic monomer of from $10^{-9}$ to $10^{-7}$M within a distance of 1 millimeter of the surface.

Alternatively or additionally, a 2-component synthetic bioelastomer comprising the chemotactic peptide of this invention and the elastic polypentapeptide or polytetrapeptide of U.S. Pat. No. 4,187,852 would act as a chemotactic elastic biopolymer which could be utilized for a variety of purposes. It is also possible to use the chemotactic peptide of this invention in a system involving natural crosslinking of synthetic bioelastomers, as is described in U.S. patent application Ser. No. 533,524, which is herein incorporated by reference. That application discloses bioelastomers which are enzymatically cross-linked by lysyl oxidase.

The above disclosure generally describes the present invention. A more complete understanding can be obtained by reference to the following specific examples, which are provided herein for purposes of illustration only and are not intended to be limiting unless otherwise specified.

EXAMPLE

The chemotactic response of fibroblasts to two nonapeptides of the invention was measured using the techniques described below.

Materials and Methods

Source of Chemicals and Materials

Dulbecco's Modified Eagle Medium (DMEM), nonessential amino acids, L-glutamine, fetal bovine serum, penicillin streptomycin solution: GIBCO, Chagrin, Ohio. Trypsin 1-300: ICN, Cleveland, Ohio. Ethylene diaminetetraacetic acid (EDTA)—sodium salt and gelatin: Sigma, St. Louis, Mo. Human serum albumin (HSA): American National Red Cross, Washington, D.C. Hematoxylin: Harleco, Gibbstown N.J. Platelet-derived growth factor (PDGF): Calbiochem., San Diego, Calif. Polycarbonate membranes: Nucleopore Corp., Pleasanton, Calif. Cellulose nitrate membranes: Millipore Corporation, Bedford, Mass.

Cells

Passage-two fetal bovine ligamentum nuchae fibroblast cell cultures were grown to confluency in 75 cm$^2$ plastic tissue culture flasks with Dulbecco's Modified Eagle (DME) medium containing 10% fetal calf serum, 2 mM L-glutamine, 0.1 mM nonessential amino acids, penicillin (100 U/ml), streptomycin (100 $\mu$g/ml). These passage-two cell cultures were obtained from passage-one cell cultures provided by R. M. Senior and R. B. Mecham (Washington University, St. Louis, Mo.). Ligamentum nuchae explants were obtained from fetal calves greater than 180 days in gestational age. Because of the possibility of platelet derived factors being present in the fetal calf serum, the cells were harvested after a 48 hour fast. At one to two days past confluency, the cells were dispersed by trypsin (0.025% trypsin, 0.1% EDTA in phosphate buffered saline, pH 7.4) and washed two times in a second DME medium containing 2 mM glutamine, 0.1 mM nonessential amino acids and 1 mg/ml human serum albumin. Cell concentration was determined with a hemocytometer and adjusted to a final concentration of $1.5 \times 10^5$ cells/ml. The cells were used as is for the chemotaxis assay.

Chemotaxis Assay

The chemotaxis experiment used a 30 hole multi-blindwell plate as an adaptation of the modified Boyden chamber. The upper and lower compartments were separated by an 8 $\mu$m polycarbonate membrane superimposed on a 0.45 $\mu$m cellulose nitrate membrane. The 8 $\mu$m membrane was pretreated with 5% gelatin to enhance fibroblast attachment. The lower compartment contained 0.24 ml of the second DME medium plus/-minus chemotactic peptides while the upper one had 0.37 ml of the second DME medium with fibroblasts. In the checkerboard assay, peptide was also added to the upper compartment. The filled plate was placed in a humidified incubator at 37° C. with 5% CO$_2$-air for 6 hours, after which the cell suspension was aspirated and the membranes were recovered, fixed in ethanol, stained in Harris' Alum hematoxylin, dehydrated in a graded series of propanol and cleared in xylene. Quantitation of cell locomotion to the area between the two membranes was done with a light microscope, fitted with a bright field objective and eye piece grid, at 400$\times$. There were 3 membrane pairs per experimental condition and 5 randomly chosen fields were examined per pair. Every experiment had a negative control, i.e. medium alone, and a positive control, i.e. platelet-derived growth factor, PDGF, in the lower compartment.

Figure 1:
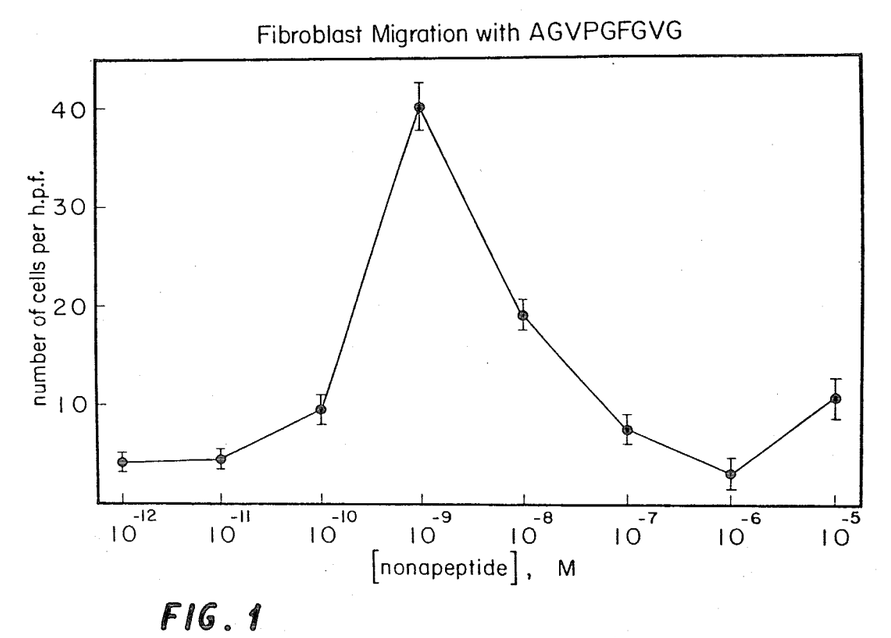
FIG. 1 is a graph of the chemotactic dose response of fibroblasts to AGVPGFGVG.
Figure 2:
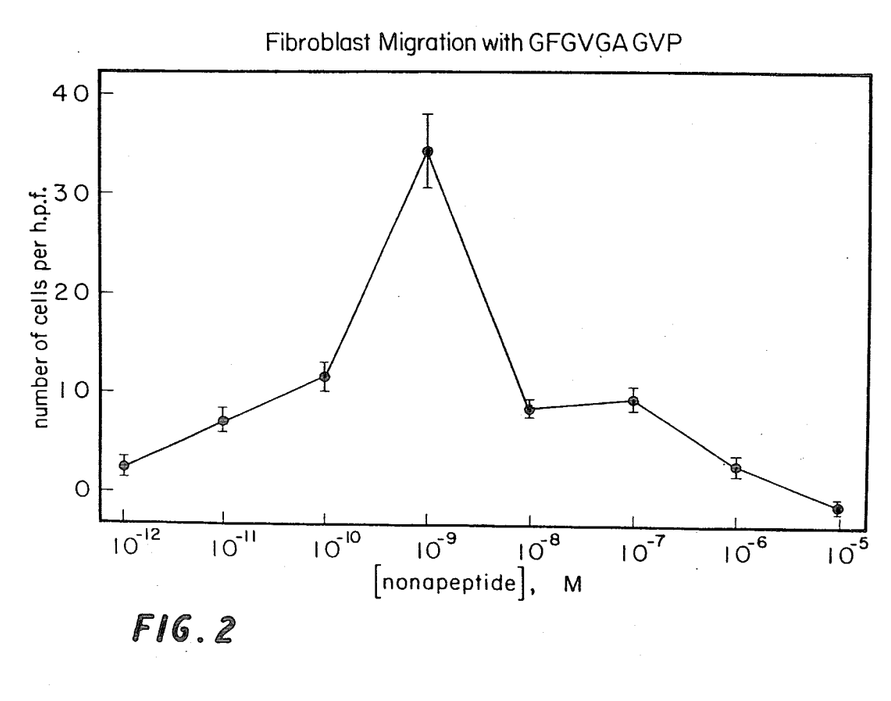
FIG. 2 is a graph of the chemotactic dose response of fibroblasts to GFGVGAGVP.
Figure 3:
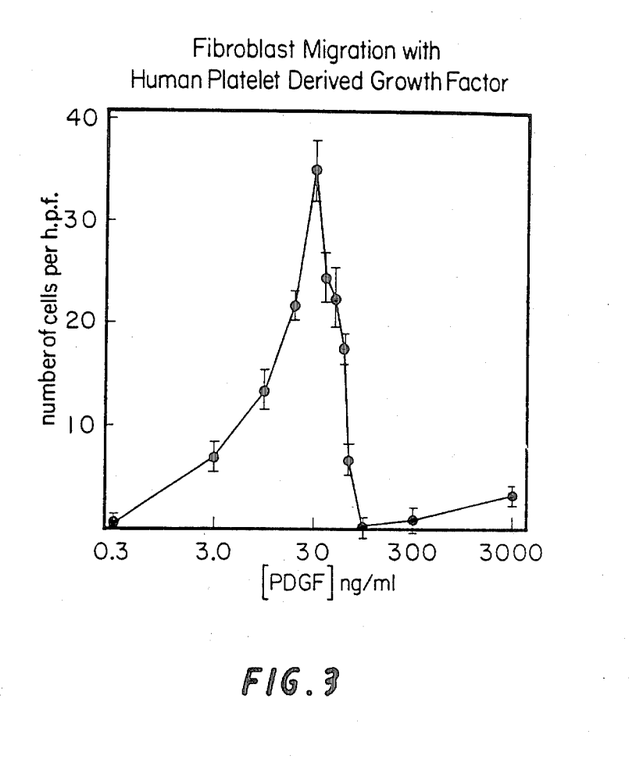
FIG. 3 is a graph of the chemotactic dose response of fibroblasts to human platelet-derived growth factor (comparison)

Number of cells per high power field are expressed in FIGS. 1 through 3 and in Tables I and II as the net number of cells that migrated through the polycarbonate membrane. The number of cells moving with medium alone in the lower compartment was subtracted from the number of cells moving in response to one of the peptides.

TABLE I

| Checkerboard Analysis of AGVPGFGVG with Fibroblasts | | | | | |
|---|---|---|---|---|---|
| | | Peptide concentration above filters (M) | | | |
| | | 0 | $10^{-10}$ | $10^{-9}$ | $10^{-8}$ |
| Peptide | 0 | (10)0 ± 1.3 | $-2 \pm 1.1$ | $-2 \pm 0.5$ | $-3 \pm 0.9$ |
| con. | $10^{-10}$ | $6 \pm 1.3$ | $-3 \pm 1.0$ | $-4 \pm 0.8$ | $2 \pm 1.8$ |
| below | $10^{-9}$ | $25 \pm 1.6$ | $3 \pm 1.7$ | $-4 \pm 0.6$ | $-2 \pm 1.1$ |

TABLE I-continued
Checkerboard Analysis of AGVPGFGVG with Fibroblasts

| | | Peptide concentration above filters (M) | | | |
|---|---|---|---|---|---|
| | | 0 | $10^{-10}$ | $10^{-9}$ | $10^{-8}$ |
| filters (M) | $10^{-8}$ | 9 ± 2.3 | 5 ± 1.6 | 5 ± 1.2 | −2 ± 1.1 |

Results are expressed as means ± S.E.M. where N = 15. Positive control, PDGF at 60 μg/ml = 21.

TABLE II
Checkerboard Analysis of GFGVGAGVP with Fibroblasts

| | | Peptide concentration above filters (M) | | | |
|---|---|---|---|---|---|
| | | 0 | $10^{-10}$ | $10^{-9}$ | $10^{-8}$ |
| Peptide conc. | 0 | (9)0 ± 1.0 | 1 ± 1.0 | 3 ± 1.2 | −2 ± 1.4 |
| | $10^{-10}$ | 13 ± 1.6 | −1 ± 0.8 | −3 ± 0.7 | −1 ± 0.8 |
| below | $10^{-9}$ | 45 ± 3.4 | 7 ± 1.8 | −2 ± 1.0 | −1 ± 1.1 |
| filters (M) | $10^{-8}$ | 21 ± 1.5 | 12 ± 1.6 | 7 ± 1.5 | 0 ± 1.50 |

Results are expresses as mean ± S.E.M. where n = 15. Positive control, PDGF at 30 μg/ml = 59.

Peptide Synthesis

Elemental analyses were carried out by MicAnal, Tuscon Az. All amino acids are of L-configuration except for glycine. Tertiary-butyloxcarbonyl (Boc)-amino acids and amino acid benzyl esters (Bzl) were purchased from Bachem, Inc., Torrance, Calif. Thin-layer chromatography was performed on silica gel plates obtained from Whatman, Inc., N.J. and mentioned as $R_f$ values in different solvent systems. $R^1$ chloroform (C), methanol (M), acetic acid (A), 95:5:3; $R_f^2$ CMA (85:15:3); $R_f^3$ CMA (75:25:3); $R_f^4$ ethyl acetate, acetic acid, ethanol (90:10:10). The hexapeptide was synthesized and purified as outlined in Senior et al., J. Cell Biol. 99: 870–874 (1984). The synthesis of the nonapeptides is carried out by solution methods and is presented in Schemes 1 and 2.

Scheme 1
Synthesis of HCO₂H.H—Ala—Gly—Val—Pro—Gly—Phe—Gly—Val—Gly—OH

Scheme 2
Synthesis of HCO₂H.H—Gly—Phe—Gly—Val—Gly—Ala—Gly—Val—Pro—OH

CF₃CO₂H·H-Gly-Val-Gly-OBzl (II): Boc-Gly-Val-Gly-OBzl (I) (10.0 g, 23.72 mmol) was stirred with 100 ml of trifluoroacetic acid (TFA) for one hour and solvent removed under reduced pressure. The residue was triturated with ether, filtered, washed with ether and dried, to give 9.4 g (yield: 91%) of the deblocked peptide.

Boc-Phe-Gly-Val-Gly-OBzl (III): Boc-Phe-OH (9.16 g, 34.54 mmol) was dissolved in 100 ml of dimethylformamide (DMF), cooled to 0° C. and N-methylmorpholine (NMM) (3.83 ml) added. The solution was cooled to −15° C. and isobutyl chloroformate (IBCF) (3.96 ml, 30 mmol) was added slowly under stirring while maintaining the temperature at −15°±1° C. After stirring at this temperature for 15 minutes, a precooled solution of II (9.4 g, 21.59 mmol) and NMM (2.4 ml) in DMF (40 ml) was added and stirring continued for two hours at ice-bath temperature. A saturated solution of $KHCO_3$ was added to bring the pH to 8.0 and stirred for an additional 30 minutes. The reaction mixture was poured into a cold 90% saturated NaCl solution (1000 ml) and the precipitate obtained was filtered, washed with satd. NaCl, $H_2O$ and dried. The peptide was crystallized from ethyl acetate to give 10 g of III (yield: 81.5%). $R_f^2$ 0.83 Anal. Calcd. for $C_{30}H_{40}N_4O_7$: C 63.35, H 7.09, N 9.85%. Found: C 62.96, H 7.37, N 9.86%.

Boc-Gly-Phe-Gly-Val-Gly-OBzl (IV): III (8.0 g, 14 mmol) was deblocked as described for II and coupled with Boc-Gly-OH by the excess mixed anhydride method and worked up as described under III to obtain the title compound in 98.6% yield, $R_f^2$ 0.75. Anal. Calcd. for $C_{32}H_{43}N_5O_8$: C 61.42, H 6.92, N 11.19%. Found: C 61.12, H 7.21, N 11.19%.

Boc-Val-Pro-Gly-Phe-Gly-Val-Gly-OBzl (VI): Boc-Val-Pro-OH (V) (29) (1.89 g, 6.02 mmol) and 1-hydroxybenzotriazole (HOBt) (0.92 g, 6.02 mmol) were taken in DMF (20 ml), cooled with ice-salt freezing mixture and reacted with 1(3-dimethylaminopropyl)-3-ethylcarbodiimide hydrochloride (EDCI) (1.15 g, 6.02 mmol) for 15 min. IV was deblocked as described under II and an ice-cold solution of this deblocked peptide (3.5 g, 5.4 mmol), NMM (0.61 ml) in DMF (20 ml) was added to the above activated acid component and stirred for two days at room temperature. Solvent was removed under reduced pressure. The residue was taken in chloroform and washed with water, 20% citric acid, water, satd. $NaHCO_3$, water, dried over anhyd. $MgSO_4$ and solvent removed under reduced pressure to give the desired peptide (3.4 g, yield: 75.7%), $R_f^1$ 0.27, $R_f^2$ 0.71 Anal. Calcd. for $C_{42}H_{59}N_7O_{10}$: C 61.36, H 7.23, N 11.93%. Found: C 61.25, H 7.66, N 12.08%.

Boc-Ala-Gly-OBzl (VII): This peptide was prepared by the mixed anhydride method as described for the synthesis of III in 81% yield, $R_f^1$ 0.24, $R_f^4$ 0.92. Anal. Calcd for $C_{17}H_{24}N_2O_5$: C 60.16, H 7.13, N 8.25%. Found: C 59.68%, H 7.17, N 8.09%.

Boc-Ala-Gly-OH (VIII): VII (16.97 g, 50 mmol) was taken in glacial acetic acid (170 ml) and hydrogenated overnight in the presence of 10% Pd/C (1.7 g) as catalyst at 40 psi. The catalyst was filtered with the aid of celite and solvent removed under reduced pressure. The residue was taken in satd. $NaHCO_3$ solution, extracted with EtOAC (3×), cooled, acidified to pH 2.0 and re-extracted with EtOAC (3×). The combined EtOAC extracts were washed with Satd, NaCl, and concentrated under reduced pressure. The residue was triturated with EtOAC: Pet. ether(1:1) and the precipitate obtained was filtered, washed with pet. ether and dried (10.9 g, yield: 87.5%), $R_f^4$ 0.52. Anal Calcd. for $C_{10}H_{18}N_2O_5 \cdot \frac{1}{2}H_2O$: C 46.50, H 7.41, N 10.84%. Found: C 46.64, H 7.41, N 10.84%.

Boc-Ala-Gly-Val-Pro-Gly-Phe-Gly-Val-Gly-OBzl (IX): VIII was coupled with the deblocked VI using EDCI/HOBt as described for the preparation of VI to give the desired peptide in 84.8% yield. $R_f^2$ 0.76, $R_f^3$ 0.28. Anal. calcd. for $C_{47}H_{67}N_9O_{12}$: C 59.22, H 7.08, N 13.22%. Found C 58.73, H 7.55, N 13.14%.

Boc-Ala-Gly-Val-Pro-Gly-Phe-Gly-Val-Gly-OH (X): The nonapeptide benzylester (IX) was hydrogenated as described under VIII to obtain the acid in quantitative yield. $R_f^3$ 0.24. Anal. calcd. for $C_{40}H_{61}N_9O_{12} \cdot H_2O$: C 55.09, H 7.16, N 14.3%. Found: C 54.69, H 7.16, N 13.81%.

$HCO_2H \cdot H$-Ala-Gly-Val-Pro-Gly-Phe-Gly-Val-Gly-OH (XI): X (20 mg, 0.023 mmol) was stirred with 95-97% formic acid (0.6 ml) for 6 hours and concentrated under reduced pressure. The residue was taken in dist. water and lyophilyzed to obtain the product in quantitative yield. $R_f^3$ 0.65. This completes synthesis of the first permutation.

Boc-Ala-Gly-Val-Pro-OBzl (XIII): To obtain the second permutation, Boc-Val-Pro-OBzl (XII) was deblocked with TFA and coupled with VIII as described under VI to obtain the protected tetrapeptide in 67.4% yield. $R_f^2$ 0.80, $R_f^4$ 0.80. Anal calc. for $C_{27}H_{40}N_4O_7$: C 60.54, H 7.52, N 10.46%. Found: C 60.80, H 7.53, N 10.56%.

Boc-Gly-Phe-Gly-Val-Gly-OH (XIV): IV was hydrogenated and worked up as described for VIII to obtain the product in quantitative yield. $R_f^3$ 0.16. Anal. calcd. for $C_{25}H_{37}N_5O_8 \cdot H_2O$: C 54.23, H 7.10, N 12.65%. Found: C 54.14, H 6.93, N 12.21%.

Boc-Gly-Phe-Gly-Val-Gly-Ala-Gly-Val-Pro-OBzl (XV): After deblocking XIII with TFA, the salt was coupled with XIV using EDCI/HOBt and worked up as for the preparation VI. The title compound was obtained in 75.5% yield. $R_f^2$ 0.57. Anal. calcd. for $C_{47}H_{67}N_9O_{12} \cdot 2H_2O$: C 57.06, H 7.23, N 12.74%. Found C 54.23, H 7.10, N 12.74%.

Boc-Gly-Phe-Gly-Val-Gly-Ala-Gly-Val-Pro-OH (XVI): The above peptide XV was hydrogenated as described for the preparation VIII to obtain the product in quantitative yield. $R_f^3$ 0.22. Anal. calcd. for $C_{40}H_{61}N_9O_{12}$: C 55.66, H 7.12, N 14.60%. Found: C 55.86, H 7.23, N 14.14%.

$NCO_2H \cdot H$-Gly-Phe-Gly-Val-Gly-Ala-Gly-Val-Pro-OH (XVII): The peptide XVI was treated with formic acid and worked up as described under XI. $R_f^3$ 0.06. This completes the synthesis of the second permutation.

Results

Figure 4:
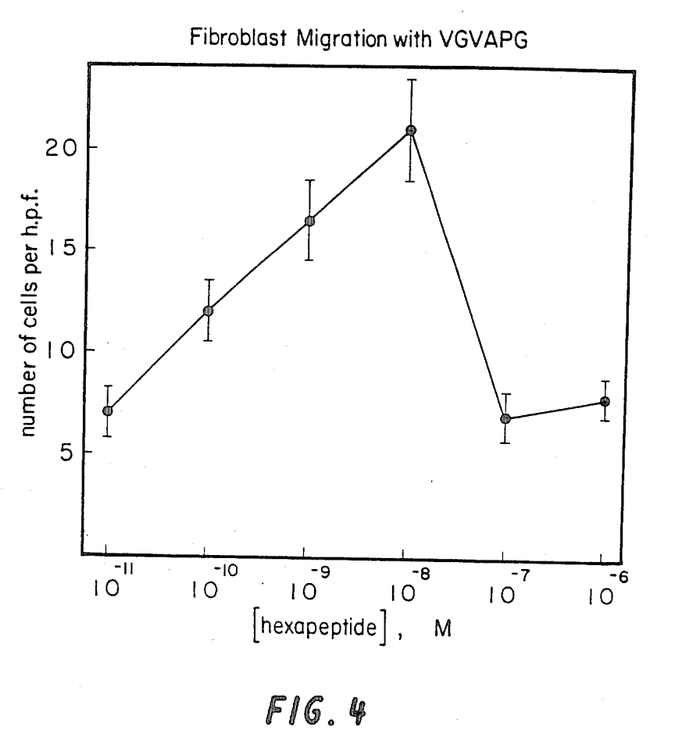
FIG. 4 is a graph of the chemotactic dose response of fibroblasts to VGVAPG (comparison).

Carbon-13 nuclear magnetic resonance spectra for the two nonapeptides demonstrated their purity. The elastin nonapeptide AGVPGFGVG (compound XI) and its premutation GFGVGAGVP are both chemoattractants for elastin synthesizing ligamentum nuchae fibroblasts. FIG. 1 shows the positive migration of fibroblasts in response to a concentration gradient ranging from $10^{-12}$ to $10^{-5}$M nonapeptide. Maximal activity was at $10^{-9}$M for AGVPGFGVG. Four such curves were run and all peaked at $10^{-9}$M. Its permutation GFGVGAGVP (compound XVII) was tested with a concentration range of $10^{-12}$ to $10^{-5}$ (FIG. 2). Again the maximal response was at $10^{-9}$M. Again, four experiments were completed and in all $10^{-9}$M represented maximal activity. FIG. 3 shows the response of the fibroblasts to human platelet derived growth factor at 0.3, 3, 10, 20, 30, 40, 50, 60, 70, 90, 300 and 3000 ng/ml. Maximum activity is at 30 ng/ml (1 nM). The hexapeptide, VGVAPG, of tropoelastin was chemotactic for fibroblasts with the peak of activity at $10^{-8}$M (FIG. 4). Two such tests were done and both peaked at $10^{-8}$ M. The "checkerboard analysis" was performed with the two nonapeptides to identify the fibroblast migration as chemotaxis. Peptide was added to the lower compartment, to the upper compartment (with the cells) or to both compartments to set up a positive, a negative or zero gradient, respectively. Tables I and II for AGVPGFGVG and GFGVGAGVP show that the cells preferentially migrated in response to a positive gradient and not to a negative gradient or to no gradient. The experiments represented by the data in Tables I and II were repeated three and two times, respectively. In all cases, the data followed the patterns seen in Tables I and II. The data demonstrate that the peptides stimulated direct (chemotaxis) rather than random (chemokinesis) migration of fibroblasts and that the peptides are true chemoattractants. Relative to the positive control of 30 μg/ml PDGF, the nonapeptides stimulated the same level of migration as PDGF.

The invention now being fully described, it will be apparent to one of ordinary skill in the art, that many changes and modifications can be made thereto without departing from the spirit or scope of the invention as set forth herein.

What is claimed as new and desired to be secured by Letters Patent of the United States is:

1. A prosthetic device wherein a surface of said device has a chemotactic peptide of the formula $B^1$-X-(AGVPGFGVG)$_n$-Y-$B^2$ wherein A is a peptide-forming residue of L-alanine:
P is a peptide-forming residue of L-proline;
G is a peptide-forming residue of glycine;
V is a peptide-forming residue of L-valine;
F is a peptide-forming residue of L-phenylalanine;
$B^1$ is H or a biocompatible N-terminal group;
$B^2$ is OH, OB$^3$ where B$^3$ is a non-toxic metal ion, or a biocompatible C-terminal group:
X is GVPGFGVG, VPGFGVG, PGFGVG, GFGVG, FGVG, GVG, VG, G or a covalent bond;
Y is AGVPGFGV, AGVPGFG, AGVPGF, AGVPG, AGVP, AGV, AG, A or a covalent bond; and
n is an interger from 1 to 100; incorporated into said surface.

2. The device of claim 1, wherein n is from 1 to 10.
3. The device of claim 1, wherein n is about 5.
4. The device of claim 1, wherein n is 1.
5. The device of claim 1, wherein said peptide is H-AGVPGFGVG-OH, H-GFGVGAGVP-OH, or a salt thereof.
6. The device of claim 1, wherein $B^1$ is H and $B^2$ is OH or OB$^3$ where B$^3$ is an alkali metal ion.
7. The device of claim 1, wherein said amount is from $10^{-9}$ to $10^{-3}$ millimols of nonamer or repeating unit per 100 cm$^2$ of said surface.
8. The device of claim 1, wherein said prosthetic device comprises a structural polypeptide.
9. The device of claim 1, wherein said chemotactic peptide is incorporated using non-covalent bonding between said chemotactic peptide and said surface.
10. The device of claim 1, wherein said surface comprises a structural peptide.